(12) United States Patent
Wang

(10) Patent No.: US 7,336,071 B2
(45) Date of Patent: Feb. 26, 2008

(54) ENHANCEMENT OF NMR VERTICAL RESOLUTION USING WALSH FUNCTION BASED INVERSION

(75) Inventor: Ning Wang, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 44 days.

(21) Appl. No.: 11/212,270

(22) Filed: Aug. 26, 2005

(65) Prior Publication Data

US 2007/0047117 A1 Mar. 1, 2007

(51) Int. Cl.
*G01V 3/00* (2006.01)
(52) U.S. Cl. ....................... 324/303; 324/300
(58) Field of Classification Search ................ 324/303, 324/300, 318, 322
See application file for complete search history.

(56) References Cited

U.S. PATENT DOCUMENTS 5,517,115 A * 5/1996 Prammer .................... 324/303
5,712,566 A 1/1998 Taicher et al. .............. 324/303
6,253,155 B1 6/2001 Hagiwara ....................... 702/9
6,331,775 B1 * 12/2001 Thern et al. ................ 324/303
6,348,792 B1 2/2002 Beard et al. ................ 324/303
6,452,388 B1 9/2002 Reiderman et al. ......... 324/303
6,717,404 B2 4/2004 Prammer .................... 324/303
7,135,862 B2 * 11/2006 Hagiwara ................... 324/303

FOREIGN PATENT DOCUMENTS

WO WO98/43064 10/1998

OTHER PUBLICATIONS

Ning Wang et al.; *The Application of Thin Bed Information Resolution of Well-Logs to Enhance the Vertical Resolution of NMR Logs*, SPE 64630, SPE International Oil and Gas Conference and Exhibition, Bejing, China, Nov. 7-10, 2000, pp. 1-7, 5 Figs., 1 Table.

* cited by examiner

*Primary Examiner*—Louis M. Arana
(74) *Attorney, Agent, or Firm*—Madan, Mossman & Sriram, P.C.

(57) ABSTRACT

NMR data are acquired using a phase-alternation of the tipping pulse. Averaged properties are estimated over a window length. The averaged properties are inverted to undo the effects of the averaging. A matrix defined in terms of Walsh functions is used in the inversion.

20 Claims, 3 Drawing Sheets

ENHANCEMENT OF NMR VERTICAL RESOLUTION USING WALSH FUNCTION BASED INVERSION

BACKGROUND OF THE INVENTION

1. Field of the Invention

The present invention relates generally to a method for improving the resolution of nuclear magnetic resonance properties of an earth formation traversed by a borehole, and more particularly, to a method for compensating for the effects of commonly used processing methods for eliminating any ringing, such as magnetoacoustic ringing, and DC offset, during a nuclear magnetic resonance measurement.

2. Background of the Art

A variety of techniques are utilized in determining the presence and estimation of quantities of hydrocarbons (oil and gas) in earth formations. These methods are designed to determine formation parameters, including among other things, the resistivity, porosity and permeability of the rock formation surrounding the wellbore drilled for recovering the hydrocarbons. Typically, the tools designed to provide the desired information are used to log the wellbore. Much of the logging is done after the well bores have been drilled. More recently, wellbores have been logged while drilling, which is referred to as measurement-while-drilling (MWD) or logging-while-drilling (LWD).

One recently evolving technique involves utilizing Nuclear Magnetic Resonance (NMR) logging tools and methods for determining, among other things, porosity, hydrocarbon saturation and permeability of the rock formations. The NMR logging tools are utilized to excite the nuclei of the liquids in the geological formations surrounding the wellbore so that certain parameters such as spin density, longitudinal relaxation time (generally referred to in the art as $T_1$) and transverse relaxation time (generally referred to as $T_2$) of the geological formations can be measured. From such measurements, porosity, permeability and hydrocarbon saturation are determined, which provides valuable information about the make-up of the geological formations and the amount of extractable hydrocarbons.

The NMR instrument also typically includes an antenna, positioned near the magnet and shaped so that a pulse of radio frequency (RF) power conducted through the antenna induces an RF magnetic field in the earth formation. The RF magnetic field is generally orthogonal to the field applied by the magnet. This RF pulse, typically called a 90° pulse, has a duration and amplitude predetermined so that the spin axes of the hydrogen nuclei generally align themselves perpendicularly both to the orthogonal magnetic field induced by the RF pulse and to the magnetic field applied by the magnet. After the 90° pulse ends, the nuclear magnetic moments of the hydrogen nuclei gradually "relax" or return to their original alignment with the magnet's field. The amount of time taken for this relaxation, referred to as $T_1$, is related to petrophysical properties of interest of the earth formation. After the 90° pulse ends, the antenna is typically electrically connected to a receiver, which detects and measures voltages induced in the antenna by precessional rotation of the spin axes of the hydrogen nuclei. The spin axes of the hydrogen nuclei gradually "dephase" because of inhomogeneities in the magnet's field and because of differences in the chemical and magnetic environment within the earth formation. Dephasing results in a rapid decrease in the magnitude of the voltages induced in the antenna. Typically, a series of 180° refocusing pulses are applied to bring the spins back into focus. Each refocusing pulse produces an echo, and from analysis of the echo train, properties of the earth formation can be estimated One problem with analysis of NMR measurements is that the signal detected by the antenna includes a parasitic, spurious ringing that interferes with the measurement of spin-echoes. One approach to reduce the effects of ringing has been to design the hardware to minimize the interaction between the electromagnetic fields and the materials in the device. For example U.S. Pat. No. 5,712,566 issued to Taicher et al. discloses a device in which the permanent magnet composed of a hard, ferrite magnet material that is formed into an annular cylinder having a circular hole parallel to the longitudinal axis of the apparatus. One or more receiver coils are arranged about the exterior surface of the magnet. An RF transmitting coil is located in the magnet hole where the static magnetic field is zero. The transmitting coil windings are formed around a soft ferrite rod. Thus, magnetoacoustic coil ringing is reduced by the configuration of the transmitting coil. Magnetorestrictive ringing of the magnet is reduced because the radial dependence of the RF field strength is relatively small due to use of the longitudinal dipole antenna with the ferrite rod. Further, magnetorestrictive ringing is reduced because the receiver coil substantially removes coupling of the receiver coil with parasitic magnetic flux due to the inverse effect of magnetostriction.

Another commonly used approach to reduce the effect of ringing is to use a so-called phase-alternated-pulse (PAP) sequence. Such a sequence is often implemented as $$RFA_{\pm x} - \tau - n \cdot (RFB_y - \tau - echo - \tau) - TW \quad (1)$$

where $RFA_{\pm x}$ is an A pulse, usually 90° tipping pulse and RFB is a B pulse, usually a 180° refocusing pulse. The ± phase of RFA is applied alternately in order to identify and eliminate systematic noises, such as ringing and DC offset through subsequent processing. By subtracting the echoes in the −sequence from the pulses in the adjoining +sequence, the ringing due to the 180° is suppressed.

PCT publication WO 98/43064 of Prammer addresses the problem of ringing caused by the excitation pulse. A dual frequency acquisition is carried out with phase alternation, the separation between the two frequencies being one fourth of the reciprocal of the delay time in acquisition between the excitation pulse and the first refocusing pulse. Averaging of the two measurements then attenuates the effect of the ringing due to the excitation and refocusing pulses.

A drawback to the averaging of phase alternated data sequence is the requirement to combine two pulse sequence cycles. Measurements made by an NMR logging tool in this manner are therefore subjected to degradation in the vertical resolution due to the logging speed, wait time between each pulse sequence, and the data acquisition time. In addition, the logging tool moves along the longitudinal axis of the borehole between each of the measurements. The problem with logging speed is exacerbated in multifrequency NMR measurements. A pulse sequence for an eight frequency logging operation may be denoted by $$\begin{aligned} &CPMG(f_1, TE_1, RFA_+, n_1) - t_1 - CPMG(f_2, TE_2, RFA_+, \\ &n_1) - t_2 - CPMG(f_8, TE_8, RFA_+, n_8) - t_8 - CPMG \\ &(f_1, TE_i, RFA_-, n_1) - t_1 - CPMG(f_2, TE_2, RFA_-, \\ &n_2) - t_2 \ldots CPMG(f_8, TE_8, RFA_-, n_8) - t_8 \end{aligned} \quad (2)$$

where $f_i$, $TE_i$ and $n_i$ are the frequency, interecho time and number of echoes for the i-th CPMG echo train. The CPMG pairs that only differ in the RFA phases are 8 sequences apart. Unless the logging speed is slowed down significantly, the two sensed volumes will be spatially separate and distinct, and the resolution of the tool is impaired.

It would be desirable to have a method of improving the resolution of NMR data that has been averaged over a depth interval. The present invention satisfies this need.

SUMMARY OF THE INVENTION

One embodiment of the invention is a method of evaluating an earth formation. Measurements indicative of a property of the formation are obtained at more than one depth. An average value over a window length of the property is determined at one or more depths. From the averaged values of the property, the property of the formation is estimated using a representation of the property by a set of basis functions over the window length. The measurements may include NMR signals that may result from a phase alternated pair of excitation pulses. The NMR signals may include spin echo signals. The property of the formation may be a porosity, bound volume irreducible, clay bound water, and/or bound volume movable. The measurements may result from excitation pulses at more than one frequency. The basis functions may be selected to match expected changes in the property and may be Walsh functions. The logging speed of a logging tool used to obtain the measurements may be selected to provide a specified resolution in the estimation of the property. Estimating the property may be done using an inversion.

Another embodiment of the invention is sn apparatus for evaluating an earth formation. The apparatus includes a logging tool conveyed into a borehole in the earth formation which makes measurements indicative of a property of the formation at more than one of depth. The apparatus also includes a processor which determines an average value over a window length of the property from the measurements and estimates from the averaged values the property of the formation, the estimation being based at least in part on representing the property by a set of basis functions over the window length. The logging tool may include a magnet and a radio-frequency (RF) antenna which pulses the earth formation and the measurements include nuclear magnetic resonance (NMR) signals. The property estimated by the processor may be a porosity, bound volume irreducible, clay bound water, and/or bound volume movable. The RF antenna may pulse the earth formation at more than one frequency. The processor may select the basis functions to match expected changes in the property. The basis functions may be Walsh functions. The apparatus may include a wireline, drilling tubular, coiled tubing or a slickline which convey the logging tool into the borehole. The processor may estimate the property by performing a matrix inversion.

Another embodiment of the invention is a computer readable medium for use with an apparatus for evaluating an earth formation. The apparatus includes a logging tool conveyed into a borehole in the earth formation, the logging tool making measurements indicative of a property of the earth formation. The medium includes instructions which enable a processor to determine an average value over a window length of the property, and, using a set of basis functions to represent the property, to estimate a value of the property. The medium may be a ROM, an EPROM, and EAROM, a flash memory and/or an Optical disk.

BRIEF DESCRIPTION OF THE DRAWINGS

For a detailed understanding of the present invention, references should be made to the following detailed description of the preferred embodiment, taken in conjunction with the accompanying drawings, in which like elements have been given like numerals, wherein.

DETAILED DESCRIPTION OF THE INVENTION

Figure 1:
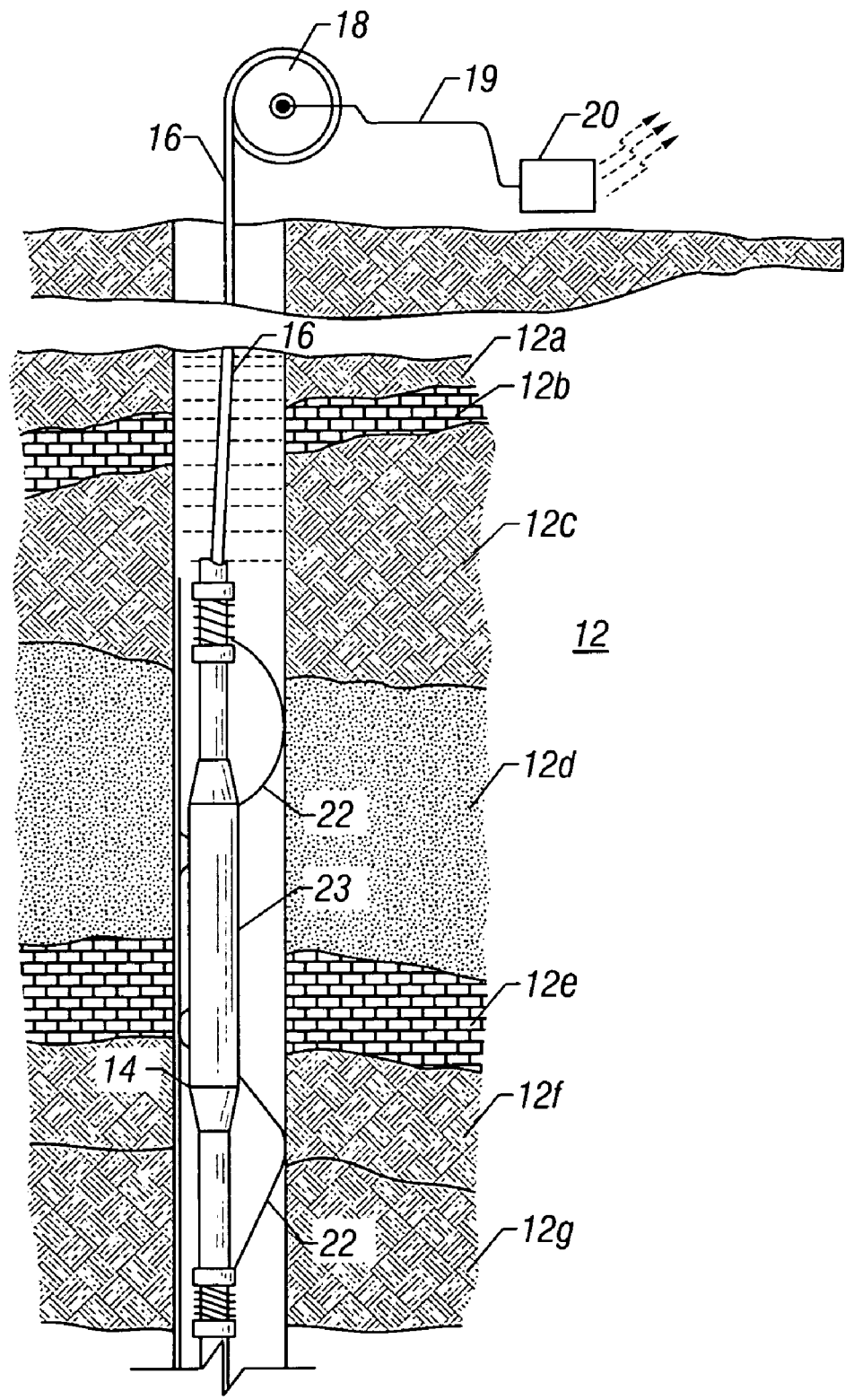
FIG. 1 (prior art) depicts diagrammatically an eccentric NMR logging tool in a borehole.

FIG. 1 (from U.S. Pat. No. 6,348,792 to Beard et al.) depicts an apparatus that is suitable for use with the present invention. This is for exemplary purposes only, and the invention can be practiced with a variety of downhole NMR devices. A borehole 10 has been drilled in a typical fashion into a subsurface geological formation 12 to be investigated for potential hydrocarbon producing reservoirs. An NMR logging tool 14 has been lowered into the hole 10 by means of a cable 16 and appropriate surface equipment represented diagrammatically by a reel 18 and is being raised through the formation 12 comprising a plurality of layers 12a through 12g of differing composition, to log one or more of the formation's characteristics. The NMR logging tool is provided with bowsprings 22 to maintain the tool in an eccentric position within the borehole with one side of the tool in proximity to the borehole wall. The permanent magnets used for providing the static magnetic field are indicated by 23 and the magnet configuration is that of a line dipole. Signals generated by the tool 14 are passed to the surface through the cable 16 and from the cable 16 through another line 19 to appropriate surface equipment 20 for processing, recording and/or display or for transmission to another site for processing, recording and/or display.

Figure 2:
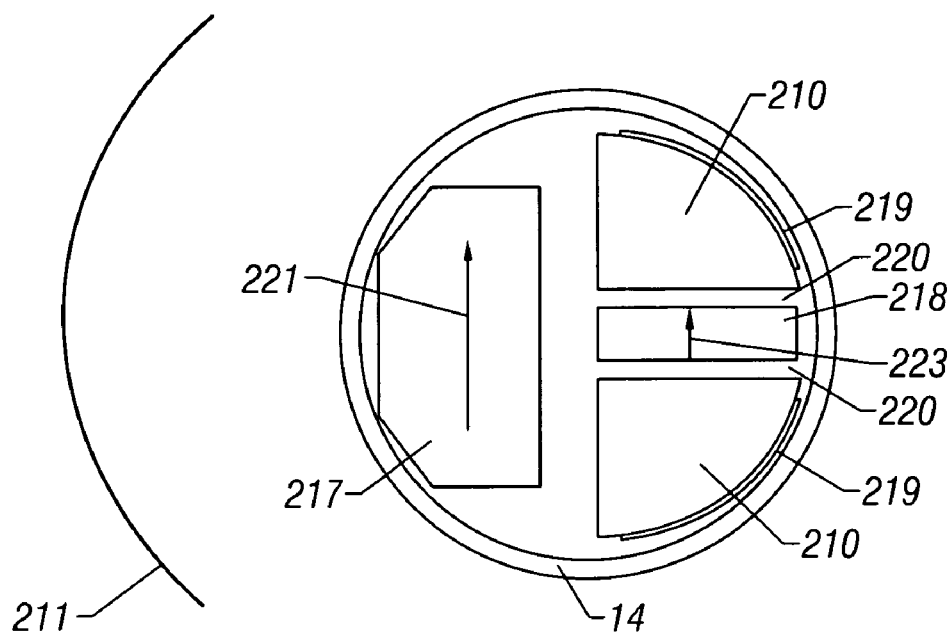
FIGS. 2, 2A, and 2B (prior art) show configurations of magnets, antenna and shield of a device suitable for use with the present invention.

FIG. 2 schematically illustrates a magnetic configuration that is suitable for use with the present invention to operate over a gradient field. The tool is described in U.S. Pat. No. 6,348,792 to Beard et al, having the same assignee as the present application and the contents of which are fully incorporated herein by reference. It should be pointed out that the method of the present invention is independent of the specific magnet configuration and can be used with either a side-looking or a centralized tool, or even the pad device. The method of the present invention does not require a gradient magnetic field. The method of the present invention can even be used with a single frequency logging tool. The tool cross-sectional view in FIG. 2 illustrates a main magnet iit, a second magnet 218, and a transceiver antenna, comprising wires 219 and core material 210. The arrows 221 and 223 depict the polarization (e.g., from the South pole to the North pole) of the main magnet 217 and the secondary magnet 218. A noteworthy feature of the arrangement shown in FIG. 2 is that the polarization of the magnets providing the static field is towards the side of the tool, rather than towards the front of the tool (the right side of FIG. 2) as in prior art devices.

The second magnet 218 is positioned to augment the shape of the static magnetic field by adding a second magnetic dipole in close proximity to the RF dipole defined by the wires 219 and the soft magnetic core 210. This moves the center of the effective static dipole closer to the RF dipole, thereby increasing the azimuthal extent of the region of examination, the desirability of which has been discussed above. The second magnet 218 also reduces the shunting effect of the high permeability magnetic core 210 on the main magnet 217: in the absence of the second magnet, the DC field would be effectively shorted by the core 210. Thus, the second magnet, besides acting as a shaping magnet for shaping the static field to the front of the tool (the side of the main magnet) also acts as a bucking magnet with respect to the static field in the core 210. Those versed in the art would recognize that the bucking function and a limited shaping could be accomplished simply by having a gap in the core; however, since some kind of field shaping is required on the front side of the tool, in a preferred embodiment of the invention, the second magnet serves both for field shaping and for bucking. If the static field in the core 210 is close to zero, then the magnetostrictive ringing from the core is substantially eliminated.

Figure 2A:
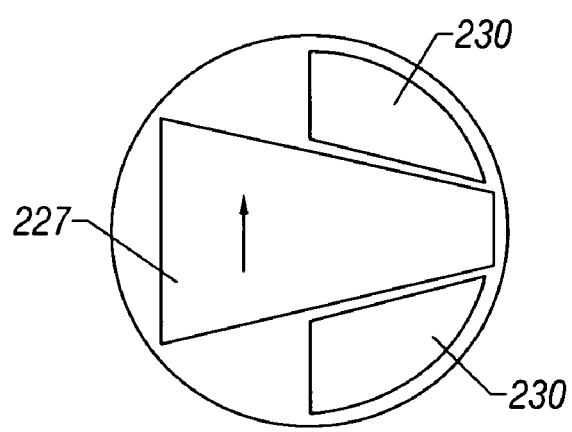
Figure 2B:
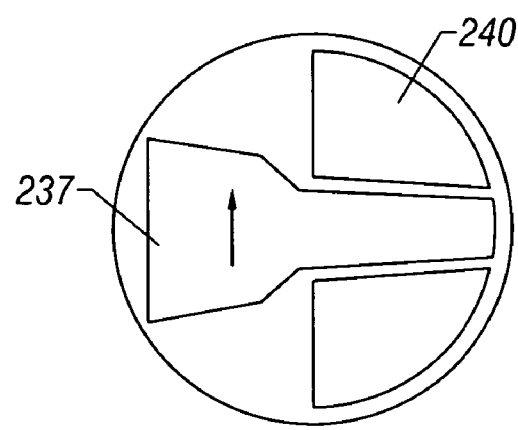

As noted above, within the region of investigation, the static field gradient is substantially uniform and the static field strength lies within predetermined limits to give a substantially uniform Larmor frequency. Those versed in the art would recognize that the combination of field shaping and bucking could be accomplished by other magnet configurations than those shown in FIG. 2. For example, FIG. 2A shows a single magnet 227 and magnetic core 230 that produces substantially the same static field as that produced by the combination of magnets 217 and 218 in FIG. 2. A substantially similar field configuration results from the arrangement in FIG. 2B with the magnet 237 and the core 240. What is being accomplished by the magnet arrangements in FIGS. 2, 2A and 2B is an asymmetry in the static magnetic field in a direction orthogonal to the direction of magnetization. In an optional embodiment of the invention (not shown) the second magnet is omitted.

Returning to FIG. 2, the transceiver wires 219 and core pieces 210 should preferably be separated as far as possible towards the sides of the tool. This separation increases the transceiver antenna efficiency by increasing the effective RF dipole of the antenna and augments the shape of the RF magnetic field isolines so that they better conform to the static magnetic field isolines. This separation is not possible in the Kleinberg design. The secondary magnet is preferably made of nonconducting material to minimize eddy currents induced by the RF field, thereby increasing the RF antenna efficiency.

The core is preferably made of a powdered soft magnetic material, other than ferrite. It preferably has a high saturation flux density and comprises particles of powdered material small enough to be transparent to the RF magnetic field. Such a material has been described in U.S. Pat. No. 6,452,388 to Reiderman et al The objective of the present invention is to "undo" the loss of resolution resulting from application of the stacking of signals. The method is based upon representing the "signal" to be recovered, i.e., a high resolution version of a formation property, in terms of Walsh functions. The functions range takes only 2 values, 1 and −1 and their domain is [0,1). Interestingly enough, the independent variable can only take discrete values, starting with 0 and with constant increment $(\frac{1}{2})^M$. Once M is determined, the functions are denoted as Wal(k, t) where k has values between 0 and $2^M-1$, and t is the independent variable. Numerically, Walsh functions can be defined iteratively:

Wal(0,t)=1;

Wal(1,t)=1 when (0<=t<½); or −1 when (½<t<=1)     (3).

Figure 3:
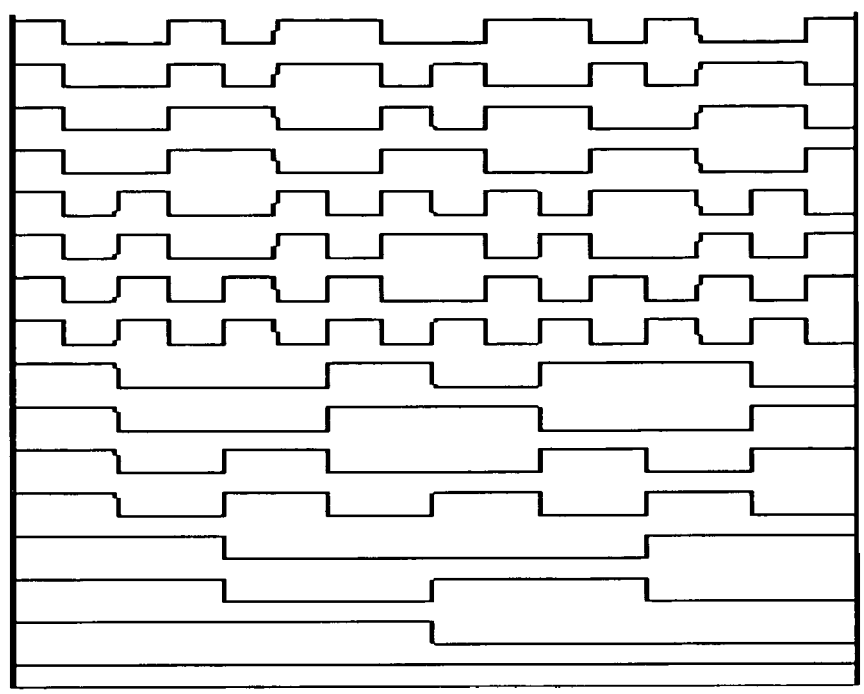
FIG. 3 shows exemplary Walsh functions used in the present invention.

Each function of order N−1 generates two functions of order N, one by contraction and repetition, the other by contraction and repetition with a change of sign. The first 16 Walsh functions are shown in FIG. 3.

Walsh functions form a complete set of orthonormal functions analogous to sines and cosines. Therefore according to the well-known mathematical theory, they can be used to represent an arbitrary function (with domain [0, 1)) in the format of series expansion. Furthermore, Walsh functions have the characteristics of step functions in that they contain a lot of high frequency components. The choice of Walsh functions is considered to be appropriate to represent the signal to be recovered particularly when formation properties have discrete step changes at layer boundaries.

NMR tools typically acquire echo trains while the tool is moving upward in the borehole. As discussed above, PAP is done first to eliminate ringing signals. It is equivalent to a 2-level averaging. As discussed above, for multifrequency acquisition, the two signals that are averaged at a particular frequency may not be consecutive in acquisition (and depth). In addition, there may be a stacking of the signals over n levels (n=2, 4, 8, 16, 32, 64, etc) depending on signal to noise ratio (SNR) of the PAPed echo trains. Finally the stacked echo trains are commonly inverted to yield $T_2$ spectra from which formation properties such as porosity, bound volume irreducible, clay bound water and bound volume movable are determined.. Due to the stacking, the vertical resolution is reduced. The present invention is based on the recognition of the fact that the operations, such as inversion, that are used to derive the formation properties are linear. Hence the operation of "unstacking" of the inverted stacked echo trains is equivalent to inverting unstacked echo trains, i.e., the operations are commutative. In what follows, a methodology for recovering a high resolution version of formation porosity is discussed. The same methodology could be used for other formation properties that are commonly determined from the NMR echo trains.

We denote by $P_m(x)$ the estimated effective porosity with depth variable x in the range of $[x_0, x_1)$ and constant sampling depth interval. Using linear mapping, $x = x_0 + t(x_1 - x_0)$, t has domain of [0,1). Therefore $P_m(t)$ is porosity defined on [0,1). It is a quantity as a result of depth level averaging over the true porosity $P_t(t)$:

$$P_m(t) = \frac{1}{2\Delta x} \int_{-\Delta x}^{\Delta x} P_t(t+\tau) d\tau. \tag{4}$$

The goal is to find out what $P_t(t)$ is. It should have more high frequency components than $P_m(t)$. $P_t(t)$ can be approximated with a Walsh expansion including the first N terms:

$$P_t(t) \approx \sum_{0}^{N-1} a_k Wal(k, t). \tag{5}$$

Substituting eqn. (5) into eqn. (4) yields:

$$P_m(t) = \sum_{0}^{N-1} a_k z_k(t), \tag{6}$$

where $$z_k(t) = \frac{1}{2\Delta x} \int_{-\Delta x}^{\Delta x} Wal(k, t + \tau) d\tau. \quad (7)$$

Discretizing eqns. (6) and (7) yields:

$$P_m(j) = \sum_{0}^{N-1} a_k z_k(k), \quad j = 0, 1, 2, \ldots, J-1, \quad (8)$$

$$z_k(j) = \frac{1}{2I+1} \sum_{i=-I}^{I} Wal(k, j+i), \quad j = 0, 1, 2, \ldots, J-1, \quad (9)$$

where J is the total number of depth levels. Note that eqn. (9) is for averaging over an odd number of depth levels. Modification for the case of an even number of depth levels would be known to those versed in the art.

Using matrix notations:

$$\vec{P}_m = [P_m(0) P_m(1) \ldots P_m(J-1)]^T \quad (10),$$

$$\vec{A} = [a_0 a_1 \ldots a_{N-1}]^T \quad (11),$$

$$\hat{G} = \begin{bmatrix} z_0(0) & z_1(0) & \cdots & z_{N-1}(0) \\ z_0(1) & z_1(1) & \cdots & z_{N-1}(1) \\ \vdots & \vdots & \vdots & \vdots \\ z_0(J-1) & z_1(J-1) & \cdots & z_{N-1}(J-1) \end{bmatrix}, \quad (12)$$

eqn. (8) can be written in a compact matrix format:

$$\vec{P}_m = \hat{G} \cdot \vec{A} \quad (13).$$

The present invention determines the matrix $\vec{A}$ by inverting eqn. (13). The matrix $\hat{G}$ has elements that are derived from the Walsh functions, which in turn are an orthonormal set of basis functions matched to the step changes expected in the earth properties. This is an ill-conditioned inversion problem. In one embodiment of the invention, a regularization method using curvature smoothing is used together with least square approach. Other regularization methods known to those versed in the art could be used. Once $\vec{A}$ is calculated, then substitution back into eqn. (5) gives an estimate of $P_f(t)$.

Figure 4:
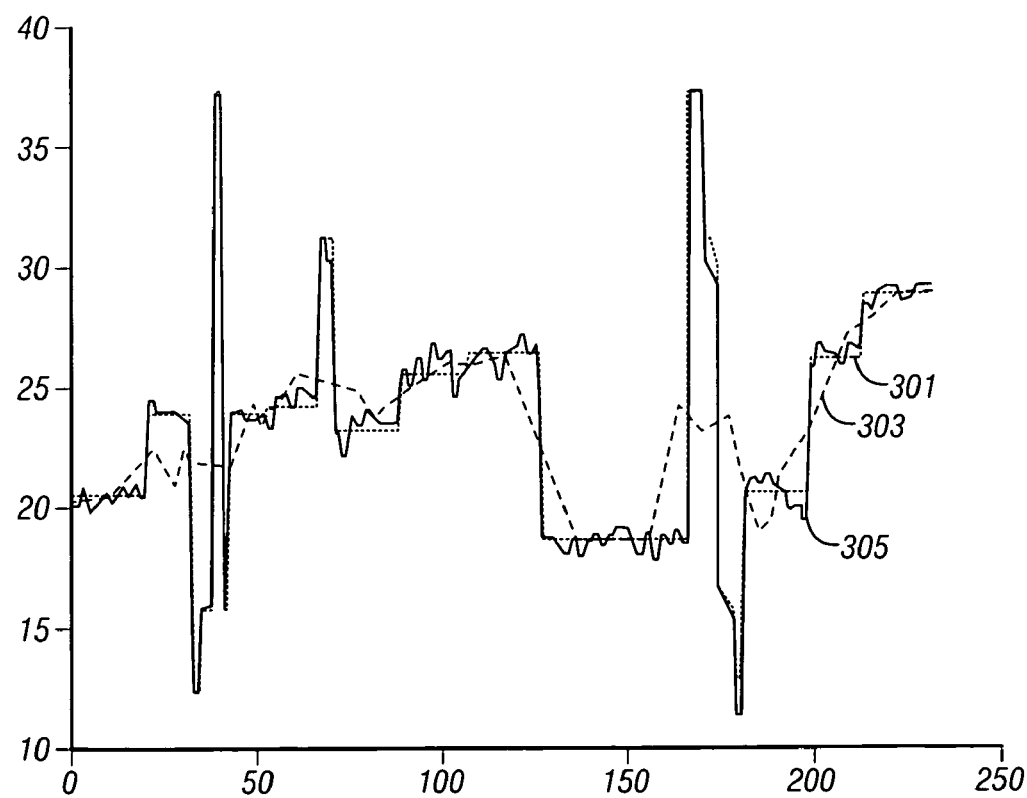
FIG. 4 shows exemplary results of using the present invention.

A formation model of effective porosity was created for 22 layers which have 232 levels of data. This is denoted as the original high resolution effective porosity model. A stacking is performed over n levels, resulting in the low resolution effective porosity, mimicking the measured effective porosity. The low resolution effective porosity was then inverted using the method described above to provide a high resolution estimate of the porosity. FIG. 4 shows an example of the results. The abscissa is the depth level and the ordinate is the porosity in percent. The discontinuous curve 301 is the layered porosity model. The smooth curve 303 is the 21 level average of 301 with additive noise of 0.5 added. The curve 305 is the result obtained by inversion. As can be seen, 305 tracks the discontinuities in the actual porosity 301 quite well.

The use of the Walsh transform for analysis of downhole data has been discussed before in U.S. Pat. No. 6,253,155 to Hagiwara. The problem addressed therein is that of compensating for the effect of tool resolution, not that of undoing the effects of processing operations such as stacking. Hagiwara teaches the application of a deconvolution filter derived by inverting a tool response correlation matrix. This is different from the present invention where a deconvolution filter is not derived.

The method of the present invention may be used for any type of logging in which signals from different depths are stacked and the processing from signals to formation properties is linear. This includes, for example, in acoustic logging, it is desirable to keep the receiver arrays as small as possible in order to improve the resolution. However, short arrays suffer from a reduced signal to noise ratio. With the method of the present invention, measurements made with short arrays that are averaged over many depths can be inverted to give velocity estimates with an improved resolution.

By the use of the present invention, it is possible to increase the logging speed for NMR measurements that are subject to PAP and multilevel stacking without significant loss of resolution.

The processing of the measurements made by the probe in wireline applications may be done by the surface processor 20 or may be done by a downhole processor (not shown). For MWD applications, the processing may be done by a downhole processor that is part of a bottomhole assembly BHA conveyed on a tubular such as a drillstring or coiled tubing. This downhole processing reduces the amount of data that has to be telemetered. Alternatively, some or part of the data may be telemetered to the surface. In yet another alternative, the measurements may be stored on a suitable memory device downhole and processed when the drillstring is tripped out of the borehole. Part of the processing may also be done at a remote location.

The operation of the logging tool may be controlled by the downhole processor and/or the surface processor. Implicit in the control and processing of the data is the use of a computer program implemented on a suitable machine readable medium that enables the processor to perform the control and processing. The machine readable medium may include ROMs, EPROMs, EAROMs, Flash Memories and Optical disks.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method of evaluating an earth formation comprising:
   (a) obtaining measurements indicative of a property of the formation at a plurality of depths;
   (b) determining an average value over a window length of the property from the measurements at each of a subset of the plurality of depths; and
   (c) estimating from the averaged values the property of the formation at a subset of the plurality of depths, the estimation being based at least in part on representing the property by a set of basis functions over the window length.

2. The method of claim 1 wherein the measurements comprise nuclear magnetic resonance (NMR) signals.

3. The method of claim 2 wherein the measurements result from a phase alternated pair (PAP) of excitation pulses.

4. The method of claim 2 wherein the measurements result from excitation pulses at a plurality of frequencies.

5. The method of claim 1 wherein the NMR signals comprise spin echo signals.

6. The method of claim 1 wherein the property of the formation is selected from the group consisting of (i) a porosity, (ii) bound volume irreducible, (iii) clay bound water, and (iv) bound volume movable.

7. The method of claim 1 wherein the basis functions comprise Walsh functions.

8. The method of claim 1 wherein the basis functions are selected to match expected changes in the property over the plurality of depths.

9. The method of claim 1 further comprising selecting a logging speed of a logging tool used for obtaining the measurements to provide a specified resolution in the estimation of the property.

10. The method of claim 1 wherein estimating the property further comprises a matrix inversion.

11. An apparatus configured to evaluate an earth formation comprising:
(a) a logging tool configured to be conveyed into a borehole in the earth formation which is configured to make measurements indicative of a property of the formation at a plurality of depths; and
(b) a processor which is configured to:
(A) determine an average value over a window length of the property from the measurements at each of a subset of the plurality of depths, and
(B) estimate from the averaged values the property of the formation at a subset of the plurality of depths, the estimation being based at least in part on representing the property by a set of basis functions over the window length.

12. The apparatus of claim 11 wherein the logging tool includes a magnet and a radio-frequency (RF) antenna configured to pulse the earth formation and wherein the measurements comprise nuclear magnetic resonance (NMR) signals.

13. The apparatus of claim 12 wherein the RF antenna is configured to the earth formation at a plurality of frequencies.

14. The apparatus of claim 11 wherein the property of the formation is selected from the group consisting of (i) a porosity, (ii) bound volume irreducible, (iii) clay bound water, and (iv) bound volume movable.

15. The apparatus of claim 11 wherein the basis functions comprise Walsh functions.

16. The apparatus of claim 11 wherein the processor is configured to select the basis functions to match expected changes in the property over the plurality of depths.

17. The apparatus of claim 11 further comprising a conveyance device which is configured to convey the logging tool into the borehole, the conveyance device selected from the group consisting of (i) a wireline, (ii) a drilling tubular, (iii) coiled tubing, and (iv) a slickline.

18. The apparatus of claim 11 wherein the processor is configured to estimate the property by further performing a matrix inversion.

19. A computer readable medium for use with an apparatus for evaluating an earth formation, the apparatus including:
(a) a logging tool conveyed into a borehole in the earth formation which makes measurements indicative of a property of the formation at a plurality of depths;
the medium comprising instructions which enable a processor to
(b) determine an average value over a window length of the property from the measurements at each of a subset of the plurality of depths, and
(c) estimate from the averaged values the property of the formation at a subset of the plurality of depths, the estimation being based at least in part on representing the property by a set of basis functions over the window length.

20. The computer readable medium of claim 19 further comprising a medium selected from the group consisting of (i) a ROM, (ii) an EPROM, (iii) an EAROM, (iv) a Flash Memory, and (v) an Optical disk.

* * * * *